US007714001B2

(12) United States Patent
Schmitt et al.

(10) Patent No.: US 7,714,001 B2
(45) Date of Patent: May 11, 2010

(54) ARYLVINYLAZACYCLOALKANE COMPOUNDS AND METHODS OF PREPARATION AND USE THEREOF

(75) Inventors: Jeffrey Daniel Schmitt, Winston-Salem, NC (US); Gary Maurice Dull, Lewisville, NC (US); Arielle Genevois-Borella, Thiais (FR); Marc Capet, Melesse (FR); Michel Cheve, Soisy sur Seine (FR)

(73) Assignee: Targacept, Inc., Winston-Salem, NC (US)

( * ) Notice: Subject to any disclaimer, the term of this patent is extended or adjusted under 35 U.S.C. 154(b) by 0 days.

(21) Appl. No.: 12/187,584

(22) Filed: Aug. 7, 2008

(65) Prior Publication Data
US 2008/0293778 A1 Nov. 27, 2008

Related U.S. Application Data

(62) Division of application No. 11/206,243, filed on Aug. 17, 2005, which is a division of application No. 10/379,868, filed on Mar. 5, 2003, now Pat. No. 7,098,331.

(51) Int. Cl.
*C07D 401/02* (2006.01)
*A61K 31/351* (2006.01)
(52) U.S. Cl. .................................. 514/343; 546/276.4
(58) Field of Classification Search .............. 546/276.4; 514/343
See application file for complete search history.

(56) References Cited

U.S. PATENT DOCUMENTS

| 4,922,901 | A | 5/1990 | Brooks et al. |
|---|---|---|---|
| 5,187,166 | A | 2/1993 | Kikuchi et al. |
| 5,583,140 | A | 12/1996 | Bencherif et al. |
| 5,585,388 | A | 12/1996 | Cosford et al. |
| 5,597,919 | A | 1/1997 | Dull et al. |
| 5,604,231 | A | 2/1997 | Smith et al. |
| 5,616,716 | A | 4/1997 | Dull et al. |
| 5,663,356 | A | 9/1997 | Ruecroft et al. |
| 5,672,601 | A | 9/1997 | Cignarella |
| 5,852,041 | A | 12/1998 | Cosford et al. |
| 6,437,138 | B1 | 8/2002 | Lin et al. |
| 2003/0092700 | A1 | 5/2003 | Czollner et al. |

FOREIGN PATENT DOCUMENTS

| EP | 0 297 858 A2 | 1/1989 |
|---|---|---|
| GB | 2 295 387 A | 5/1996 |
| WO | WO 94/08992 | 4/1994 |
| WO | WO 96/31475 | 10/1996 |
| WO | WO 96/40682 | 12/1996 |
| WO | WO 97/46554 | 12/1997 |
| WO | WO 99/21834 | 5/1999 |
| WO | WO 00/75110 | 12/2000 |
| WO | WO 01/19817 | 3/2001 |
| WO | WO 01/32264 | 5/2001 |
| WO | WO 02/12245 | 2/2002 |
| WO | WO 03/008559 | 1/2003 |

OTHER PUBLICATIONS

Damasio, Alzheimer's Disease and Related Dementias, Cecil Textbook of Medicine, 20th Edition, vol. 2, pp. 1992-1996, 1996.*
Layzer, Degenerative Diseases of the Nervous System, Cecil Textbook of Medicine, 20th Edition, vol. 2, pp. 2050-2057, 1996.*
Romanelli et al., Cholinergic Nicotinic Receptors: Competitive Ligands, Allosteric Modulators, and Their Potential Applications, Medicinal Research Reviews, vol. 23, No. 4, pp. 393-426, 2003.*
Arneric, S., et al., "Preclinical Pharmacology of ABT-418: A Prototypical Cholinergic Channel Activator for the Potential Treatment of Alzheimer's Disease," *CNS Drug Rev.*, 1(1): 1-26 (1995).
Arneric, S., et al., "Cholinergic channel modulators as a novel therapeutic strategy for Alzheimer's disease," *Exp. Opin. Invest. Drugs*, 5(1): 79-100 (1996).
Arneric, et al., Neuronal nicotinic receptors: A perspective on two decades of drug discovery research, *Biochemical Pharmacology*, 74: 1092-1101(2007).
Bannon, A. W., et al., "Broad-Spectrum, Non-Opioid Analgesic Activity by Selective Modulation of Neuronal Nicotinic Acetylcholine Receptors," *Science*, 279: 77-80 (1998).
Bencherif, M., and J. D. Schmitt, "Targeting Neuronal Nicotinic Receptors: a Path to New Therapies," *Current Drug Targets*, 1(4): 349-357 (2002).
Bencherif, M., and R.J. Lukas, "Ligand Binding and Functional Characterization of Muscarinic Acetylcholine Receptors on the TE671/RD Human Cell Line," *J. Pharmacol. Exp. Ther.*, 257(3): 946-953 (1991).
Bencherif, M., et al., "RJR-2403: A Nicotinic Agonist with CNS Selectivity I: In Vitro Characterization," *J. Pharmacol. Exper. Therapeutics*, 279(3): 1413-1421 (1996).

(Continued)

*Primary Examiner*—Deepak Rao
(74) *Attorney, Agent, or Firm*—Womble Carlyle Sandridge & Rice, PLLC; Amy H. Fix

(57) ABSTRACT

Novel vinylazacycloalkane compounds of Formula (I) are disclosed. The compounds are ligands of various nAChRs. The compounds and their pharmaceutically acceptable salts can be used to prepare pharmaceutical compositions and/or medicaments intended to prevent or treat disorders associated with dysfunction of nAChRs, especially within the central nervous system or the gastrointestinal system. Examples of types of disorders that can be treated include neurodegenerative disorders, including central nervous system disorders such as Alzheimer's disease, cognitive disorders, motor disorders such as Parkinson's disease, drug addiction, behavioral disorders and inflammatory disorders within the gastrointestinal system. The compounds can also serve as analgesics in the treatment of acute, chronic or recurrent pain.

2 Claims, No Drawings

OTHER PUBLICATIONS

Bencherif M. and R.J. Lukas, "Differential Regulation of Nicotinic Acetylcholine Receptor Expression by Human TE671/RD Cells Following Second Messenger Modulation and Sodium Butyrate Treatments," *Mol Cell Neurosci.*, 2(1): 52-65 (1991).

Brioni, J.D., et al., "The Pharmacology of (−)-Nicotine and Novel Cholinergic Channel Modulators," *Adv. Pharmacol.*, 37: 153-214 (1997).

Cheng, Yung-Chi, and W.H. Prusoff, "Relationship Between the Inhibition Constant ($K_I$) and the Concentration of Inhibitor which Causes 50 per Cent inhibition ($I_{50}$) of an Enzymatic Reaction," *Biochem. Pharmacol.*, 22(23):3099-3108 (1973).

Chiari, A., et al., "Sex Differences in Cholinergic Analgesia I: A Supplemental Nicotinic Mechanism in Normal Females," *Anesthesiology*, 91(5): 1447-1454 (1999).

Damaj, M.I., et al., "Antinociceptive and Pharmacological Effects of Metanicotine, a Selective Nicotinic Agonist," *J. Pharmacol. Exp. Ther.*, 291(1): 390-398 (1999).

Damaj, M.I., et al., "Analgesic Activity of Metanicotine, A Selective Nicotinic Agonist," *Society for Neuroscience*, 23: 669 Abstract 266.9 (1997).

Davies, A.R.L., et al., "Characterisation of the binding of [$^3$H]methyllycaconitine: a new radioligand for labeling α7-type neuronal nicotinic acetylcholine receptors," *Neuropharmacol.*, 38: 679-690 (1999).

Decina, P., et al., "Cigarette Smoking and Neuroleptic-Induced Parkinsonism," *Biol. Psychiatry*, 28(6): 502-508 (1990).

Gibson, S. et al., "Principal Components Describing Biological Activities and Molecular Diversity of Heterocyclic Aromatic Ring Fragments," *J. Med. Chem.*, 39: 4065-4072 (1996).

Hall, G.H. and D.M. Turner, "Effects of Nicotine on the Release of $^3$H-Noradrenaline from the Hypothalamus," *Biochemical Pharmacology*, 21: 1829-1838 (1972).

Hamon, M., "Neuropharmacology of anxiety: perspectives and prospects," *TiPS*, 15: 36-39 (1994).

Hansch, C., et al., "The Parabolic Dependence of Drug Action upon Lipophilic Characteras Revealed by a Study of Hypnotics," *J. Med. Chem.*, 11(1): 1-11 (1967).

Harsing, Jr., L.G., et al., "Dopamine Efflux from Striatum After Chronic Nicotine: Evidence for Autoreceptor Desensitization," *J. Neurochem.*, 59: 48-54 (1992).

Hery, F., et al., "Control of the Release of Newly Synthetized $^3$H-5-Hydroxytryptamine by Nicotinic and Muscarinic Receptors in Rat Hypothalamic Slices," *Naunyn-Schmiedeberg's Arch. Pharmacol.*, 296: 91-97 (1977).

Holladay, M.W., et al., "Neuronal Nicotinic Acetylcholine Receptors as Targets for Drug Discovery," *J. Med. Chem.*, 40(26): 4169-4194 (1997).

Hoyer, D. and H.W.G.M. Boddeke, "Partial agonists, full agonists, antagonists: dilemmas of definition," *TiPS Reviews*, 14: 270-275 (1993).

Lavand'homme, P., and J.C. Eisenach, "Sex Differences in Cholinergic Analgesia II: Differing Mechanisms in Two Models of Allodynia," *Anesthesiology*, 91(5): 1455-1461 (1999).

Levin, E.D., and A.H. Rezvani, "Nicotinic Treatment for Cognitive Dysfunction," *Current Drug Targets: CNS and Neurological Disorders*, 1(4): 423-431(2002).

Lippiello, P.M., et al., "RJR-2403: A Nicotinic Agonist with CNS Selectivity II. In Vivo Characterization," *J. P. E. T.*, 279(3): 1422-1429 (1996).

Lukas, R.J., and M.J. Cullen, "An Isotopic Rubidium Ion Efflux Assay for the Functional Characterization of Nicotinic Acetylcholine Receptors on Clonal Cell Lines," *Anal. Biochem.*, 175(1): 212-218 (1988).

Lukas, R.J., "Pharmacological Distinctions between Functional Nicotinic Acetylcholine Receptors on the PC12 Rat Pheochromocytoma and the TE671 Human Medulloblastoma," *J. Pharmacol. Exp. Ther.*, 251(1): 175-182 (1989).

Lukas R.J., et al., "Characterization of Nicotinic Acetylcholine Receptors Expressed by Cells of the SH-SY5Y Human Neuroblastoma Clonal Line," *Molec Cellular Neurosci.*, 4(1): 1-12 (1993).

Luther, et al., "A Muscle Acetylcholine Receptor is Expressed in the Human Cerebellar Medulloblastoma Cell Line," *J. Neurosci.*, 9(3): 1082-1096 (1989).

Marks, M.J., et al., "Nicotinic Binding Sites in Rat and Mouse Brain: Comparison of Acetylcholine, Nicotine, and α-Bungarotoxin," *Mol. Pharmacol.*, 30(5): 427-436 (1986).

O'Neill, M.J., et al., "The Role of Neuronal Nicotinic Acetylcholine Receptors in Acute and Chronic Neurodegeneration," *Current Drug Targets: CNS and Neurological Disorders*, 1(4): 399-411(2002).

Onaivi, E.S., et al., "Chronic Nicotine Reverses Age-Associated Increases in Tail-Flick Latency and Anxiety in Rats," *Life Sciences*, 54(3): 193-202 (1993).

Oswald, R.E., et al., "Characterization of nicotinic acetylcholine receptor channels of the TE671 human medulloblastoma clonal line," *Neurosci. Lett.*, 96: 207-212 (1989).

Pomerleau, O.F., et al., "The Effects of Cigarette Smoking on Pain and Anxiety," *Addictive Behaviors*, 9: 265-271 (1984).

Pullan, R.D., et al. "Transdermal Nicotine for Active Ulcerative Colitis," *New England J. Med.*, 330(12): 811-815 (1994).

Rapier, C., et al., "Stereoselective Nicotine-Induced Release of Dopamine from Striatal Synaptosomes: Concentration Dependence and Repetitive Stimulation," *J. Neurochem.*, 50(4): 1123-1130 (1988).

Rapier, C., et al., "Nicotinic Modulation of [$^3$H]Dopamine Release from Striatal Synaptosomes: Pharmacological Characterisation," *J. Neurochem.*, 54(3): 937-45 (1990).

Robinson, Medical Therapy of Inflammatory Bowel Disease for the 21$^{st}$ Century, *Eur. J. Surg.; Suppl.* 582: 90-98 (1998).

Romano, C., and A. Goldstein, "Stereospecific Nicotine Receptors on Rat Brain Membranes," *Science*, 210: 647-650 (1980).

Rowell, P.P. and D.L. Winkler, "Nicotinic Stimulation of [$^3$H] Acetylcholine Release from Mouse Cerebral Cortical Synaptosomes," *J. Neurochem.*, 43(6): 1593-1598 (1984).

Sanberg, P.R., et al., "Nicotine Potentiation of Haloperidol-Induced Catalepsy: Striatal Mechanisms," *Pharmacol. Biochem. & Behavior*, 46: 303-307 (1993).

Sandor, N.T., et al. "Effect of nicotine on dopaminergic-cholinergic interaction in the striatum," *Brain Res.*, 567: 313-316 (1991).

Schmitt, J.D., and M. Bencherif, "Chapter 5. Targeting Nicotinic Acetylcholine Receptors: Advances in Molecular Design and Therapies," *Ann. Rep. Med. Chem.*, 35: 41-51(2000).

Sjak-Shie, N.N. and E.M. Meyer, "Effects of chronic nicotine and pilocarpine administration on neocortocal neuronal density and [$^3$H]GABA uptake in nucleus basalis lesioned rats," *Brain Res.*, 624: 295-298 (1993).

Stratton, M.R., et al., "Characterization of the human cell line TE671," *Carcinogenesis*, 10(5): 899-905 (1989).

Toth, E., et al., "Effect of Nicotine of Extracellular Levels of Neurotransmitters Assessed by Microdialysis in Various Brain Regions: Role of Glutamic Acid," *Neurochem. Res.*, 17(3): 265-270 (1992).

Tripathi, H.L., et al., "Nicotine-Induced Antinociception of Rats and Mice: Correlation with Nicotine Brain Levels," *J. Pharmacol. Exp. Ther.*, 221(1): 91-96 (1982).

Vizi, E.S., "Acetylcholine release from guinea-pig ileum by parasympathetic ganglion stimulants and gastrin-like polypeptides," *Br. J. Pharmac.*, 47: 765-777 (1973).

Wagner, B., et al., "Does Smoking Reduce the Risk of Neuroleptic Parkinsonoids?," *Pharmacopsychiat.*, 21: 302-303 (1988).

Whiting, P.J., et al., "Expression of nicotinic acetylcholine receptor subtypes in brain and retina," *Brain Res Mol Brain Res.*, 10(1): 61-70 (1991).

Whiting, P.J., et al., "Functional acetylcholine receptor in PC12 cells reacts with a monoclonal antibody to brain nicotinic receptors," *Nature*, 327(6122): 515-518(1987).

Williams, M., et al., "Neuronal Nicotinic Acetylcholine Receptors," *DN&P*, 7(4): 205-223 (1994).

Silva, N.M., et al., "New isoxazole derivatives designed as nicotinic acetylcholine receptor ligand candidates," *Eur. J. Med. Chem.*, 37: 163-170 (2002).

International Search Report (PCT/US2004/006530, dated Aug. 13, 2004).

\* cited by examiner

ARYLVINYLAZACYCLOALKANE COMPOUNDS AND METHODS OF PREPARATION AND USE THEREOF

CROSS-REFERENCE TO RELATED APPLICATIONS

The present application is a divisional of U.S. application Ser. No. 11/206,243, filed Aug. 17, 2005, which is a divisional of U.S. application Ser. No. 10/379,868, filed Mar. 5, 2003, now U.S. Pat. No. 7,098,331, each of which is incorporated herein by reference.

FIELD OF THE INVENTION

The present invention relates to pharmaceutical compositions incorporating compounds capable of affecting nicotinic acetylcholinergic receptors (nAChRs), for example, as modulators of specific nicotinic receptor subtypes. The present invention also relates to methods for treating a wide variety of conditions and disorders, particularly those associated with dysfunction of the central and autonomic nervous systems.

BACKGROUND OF THE INVENTION

Nicotine has been proposed to have a number of pharmacological effects. See, for example, Pullan et al., N. Engl. J. Med. 330:811-815 (1994). Certain of those effects can be related to effects upon neurotransmitter release. Release of acetylcholine, dopamine, norepinephrine, serotonin and glutamate upon administration of nicotine has been reported (Rowell et al., J. Neurochem. 43:1593 (1984); Rapier et al., J. Neurochem. 50:1123 (1988); Sandor et al., Brain Res. 567: 313 (1991) and Vizi, Br. J. Pharmacol. 47:765 (1973); Hall et al., Biochem. Pharmacol. 21:1829 (1972); Hery et al., Arch. Int. Pharmacodyn. Ther. 296:91 (1977); and Toth et al., Neurochem Res. 17:265 (1992)). Confirmatory reports and additional recent studies have included the modulation in the Central Nervous System (CNS) of glutamate, nitric oxide, GABA, takykinins, cytokines and peptides (reviewed in Brioni et al., Adv. Pharmacol. 37:153 (1997)). In addition, nicotine reportedly potentiates the pharmacological behavior of certain pharmaceutical compositions used to treat certain disorders. See, for example, Sanberg et al., Pharmacol. Biochem. & Behavior 46:303 (1993); Harsing et al., J. Neurochem. 59:48 (1993) and Hughes, Proceedings from Intl. Symp. Nic. S40 (1994). Furthermore, the neuroprotective effects of nicotine have been proposed, see, for example, Sjak-shie et al., Brain Res. 624:295 (1993). Various other beneficial pharmacological effects have also been proposed. See, for example, Decina et al., Biol. Psychiatry 28:502 (1990); Wagner et al., Pharmacopsychiatry 21:301 (1988); Pomerleau et al., Addictive Behaviors 9:265 (1984); Onaivi et al., Life Sci. 54(3):193 (1994); Tripathi et al., J. Pharmacol. Exp. Ther. 221:91 (1982) and Hamon, Trends in Pharmacol. Res. 15:36 (1994).

Various compounds that target nAChRs have been reported as being useful for treating a wide variety of conditions and disorders. See, for example, Williams et al., DN&P 7(4):205 (1994); Arneric et al., CNS Drug Rev. 1(1):1 (1995); Arneric et al., Exp. Opin. Invest. Drugs 5(1):79 (1996); Bencherif et al., J. Pharmacol. Exp. Ther. 279:1413 (1996); Lippiello et al., J. Pharmacol. Exp. Ther. 279:1422 (1996); Damaj et al., J. Pharmacol. Exp. Ther. 291:390 (1999); Chiari et al., Anesthesiology 91:1447 (1999); Lavand'homme and Eisenbach, Anesthesiology 91:1455 (1999); Holladay et al., J. Med. Chem. 40(28): 4169 (1997); Bannon et al., Science 279: 77 (1998); PCT WO 94/08992, PCT WO 96/31475, PCT WO 96/40682, and U.S. Pat. No. 5,583,140 to Bencherif et al., U.S. Pat. No. 5,597,919 to Dull et al., U.S. Pat. No. 5,604,231 to Smith et al. and U.S. Pat. No. 5,852,041 to Cosford et al. Nicotinic compounds are reported as being particularly useful for treating a wide variety of CNS disorders. Indeed, a wide variety of nicotinic compounds have been reported to have therapeutic properties. See, for example, Bencherif and Schmitt, Current Drug Targets: CNS and Neurological Disorders 1(4): 349-357 (2002), Levin and Rezvani, Current Drug Targets: CNS and Neurological Disorders 1(4): 423-431 (2002), O'Neill, et al., Current Drug Targets: CNS and Neurological Disorders 1(4): 399-411 (2002), U.S. Pat. No. 5,187,166 to Kikuchi et al., U.S. Pat. No. 5,672,601 to Cignarella, PCT WO 99/21834 and PCT WO 97/40049, UK Patent Application GB 2295387 and European Patent Application 297,858.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses, and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a deficiency of acetylcholine, dopamine, norepinephrine and/or serotonin. Relatively common CNS disorders include presenile dementia (early-onset Alzheimer's disease), senile dementia (dementia of the Alzheimer's type), micro-infarct dementia, AIDS-related dementia, vascular dementia, Creutzfeld-Jakob disease, Pick's disease, Parkinsonism including Parkinson's disease, Lewy body dementia, progressive supranuclear palsy, Huntington's chorea, tardive dyskinesia, hyperkinesia, epilepsy, mania, attention deficit disorder, anxiety, dyslexia, schizophrenia, depression, obsessive-compulsive disorders and Tourette's syndrome.

There exist subtypes of nAChRs in both the central and peripheral nervous systems, but the distribution of subtypes is heterogeneous. For instance, the subtypes which are predominant in vertebrate brain are α4β2, α7, and α3β2, whereas those which predominate at the autonomic ganglia are α3β4 and those of neuromuscular junction are α1β1δγ and α1β1δε (see for instance Dwoskin et al., Exp. Opin. Ther. Patents 10: 1561 (2000) and Schmitt and Bencherif, Annual Reports in Med. Chem. 35: 41 (2000)). A limitation of some nicotinic compounds is that they elicit various undesirable pharmacological effects because of their interaction with nAChRs in peripheral tissues (for example, by stimulating muscle and ganglionic nAChR subtypes). It would be desirable to have compounds, compositions and methods for preventing and/or treating various conditions or disorders (e.g., CNS disorders), including alleviating the symptoms of these disorders, where the compounds exhibit nicotinic pharmacology with a beneficial effect on the CNS nAChRs (e.g., upon the functioning of the CNS), but without significant associated effects on the peripheral nAChRs (compounds specific for CNS nAChRs). It would further be highly desirable to provide compounds, compositions and methods that affect CNS function without significantly affecting those receptor subtypes which have the potential to induce undesirable side effects (e.g., appreciable activity at cardiovascular and skeletal muscle sites). The present invention provides such compounds, compositions and methods.

SUMMARY OF THE INVENTION

The present invention relates to the vinylazacycloalkane compounds of Formula (I):

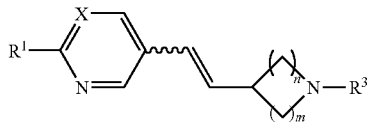

wherein:
the wavy line represents variable geometry (E or Z) about the double bond;
X is nitrogen or C—R²;
R¹ is hydrogen, $C_{1-6}$-alkyl, halogen, —OR⁴, —NR⁴R⁵, or —SR⁴ when X is C—R² and hydrogen, $C_{1-6}$ alkyl, —OR⁴, or —NR⁴R⁵ when X is nitrogen;
R² is hydrogen, $C_{1-6}$-alkyl, aryl, aryl-$C_{1-6}$-alkyl, $C_{1-6}$-alkyl-aryl, heteroaryl, heteroaryl-$C_{1-6}$-alkyl, heterocyclyl, heterocycloalkyl, cycloalkyl, polycycloalkyl, —OR⁶, —NR⁶R⁷, —SR⁶, —SOR⁶, or —SO₂R⁶, each of which can optionally be substituted with 1 or more substituents selected from halogen, —CN, —NO₂, —NH₂, —OH, —OR⁶, —COOH, —C(O)R⁶, —O—C(O)R⁶, —NR⁶R⁷, —NHC(O)R⁶, —C(O)NR⁶R⁷, —SR⁶, —S(O)R⁶, —SO₂R⁶, —NHSO₂R⁶, —SO₂NR⁶R⁶, —C(S)NR⁶R⁶, —NHC(S)R⁶, —O—SO₂R⁶, aryl, heteroaryl, formyl, trifluoromethyl, trifluoromethylsulfanyl, trifluoromethoxy, and $C_{1-6}$ alkyl;

R³ is hydrogen, $C_{1-6}$-alkyl, aryl-$C_{1-6}$-alkyl, heteroaryl $C_{1-6}$-alkyl, heterocyclyl, heterocycloalkyl, cycloalkyl or polycycloalkyl;
m is between 1 and 4;
n is between 1 and 3;
R⁴ and R⁵ are, independently, hydrogen or $C_{1-6}$-alkyl;
R⁶ and R⁷ are, independently, hydrogen, $C_{1-6}$-alkyl, aryl, aryl-$C_{1-6}$-alkyl, heteroaryl, heteroaryl-$C_{1-6}$-alkyl, heterocyclyl, heterocyclylalkyl, cycloalkyl or polycycloalkyl, each of which can optionally be substituted with one or more substituents selected from the group consisting of halogen, $C_{1-6}$ alkyl, $C_{1-6}$ alkoxy, —CN, —NO₂, —NH₂, —OH, —COOH, —COO—$C_{1-6}$ alkyl, —CONH₂, formyl, trifluoromethyl and trifluoromethoxy,
wherein the $C_{1-6}$-alkyl, heterocyclyl, heteroaryl and aryl groups can be substituted with from 1-6 substituents selected from the group consisting of F, Cl, Br, I, R⁸, —NR⁸R⁹, —CF₃, —CN, —NO₂, —C₂R⁸, —N₃, —SO₂CH₃, —OR⁸, —SR⁸, —C(=O)NR⁸R⁹, —NR⁸C(=O)R⁸, —C(=O)R⁸, —C(=O)OR⁸, —(CH₂)$_q$OR⁸, —OC(=O)R⁸, —OC(=O)NR⁸R⁹ and —NR⁸C(=O)OR⁸,
where R⁸ and R⁹ are individually hydrogen or lower alkyl (e.g., $C_1$-$C_6$ alkyl, preferably methyl, ethyl, isopropyl or isobutyl), an aromatic group-containing species or a substituted aromatic group-containing species (substituted with one or more of the above substituents).
Either R⁶ and R⁷ or R⁸ and R⁹ can also form a $C_{1-10}$ cycloalkyl functionality (e.g., cyclopropyl cyclobutyl, cyclopentyl, cyclohexyl, cycloheptyl and adamantyl). Representative aromatic group-containing species include pyridyl, quinolinyl, pyrimidinyl, phenyl and benzyl (where any of the foregoing can be suitably substituted with at least one substituent group as defined above, specifically including lower alkyl, halo, and/or amino substituents). Other representative aromatic ring systems are set forth in Gibson et al., J. Med. Chem. 39:4065 (1996).

Isomers, mixtures, including racemic mixtures, enantiomers, diastereomers and tautomers of these compounds as well as pharmaceutically acceptable salts thereof, are also included.

The present invention relates more particularly to derivatives of Formula (I) in which:
the geometry at the double bond is E;
X is N or C—R²;
R¹ is hydrogen;
R² is —OR⁶;
R³ is hydrogen;
n is 1;
m is 2; and
R⁶ is a alkyl, aryl or heterocyclyl; and
isomers thereof, mixtures thereof, including racemic mixtures, enantiomers, diastereomers and tautomers thereof, and pharmaceutically acceptable salts thereof, and to their use as ligands of nAChRs.

The compounds of Formula (I) and their pharmaceutically acceptable salts can be used to prepare pharmaceutical compositions and/or medicaments intended to prevent the disorders or to treat the diseases associated with dysfunction of the nAChRs, especially within the central nervous system or the gastrointestinal system. The term "to treat" can cover both beneficial effects on the symptoms and/or on the course of the condition under consideration.

Examples of types of disorders that can be treated include neurodegenerative disorders, including central nervous system disorders such as Alzheimer's disease and other dementia, motor disorders such as Parkinson's disease, drug addiction, behavioral disorders and inflammatory disorders within the gastrointestinal system. The compounds can also serve as analgesics, for example, in the treatment of acute, chronic or recurrent pain.

DETAILED DESCRIPTION OF THE INVENTION

The compounds, compositions and methods described herein will be better understood with reference to the following preferred embodiments. The following definitions will be useful in defining the scope of the invention:

As used herein, "aromatic" refers to 3 to 10, preferably 5 and 6-membered ring aromatic and heteroaromatic rings.

As used herein, "aromatic group-containing species" refer to moieties that are or include an aromatic group. Accordingly, phenyl and benzyl moieties are included in this definition, as both are or include an aromatic group.

As used herein, $C_{1-6}$ alkyl radicals (lower alkyl radicals) contain from 1 to 6 carbon atoms in a straight or branched chain, and also include $C_{3-6}$ cycloalkyl moieties and alkyl radicals that contain $C_{3-6}$ cycloalkyl moieties.

As used herein, $C_{1-6}$ alkoxy radicals contain from 1 to 6 carbon atoms in a straight or branched chain, and also include $C_{3-6}$ cycloalkyl and alkoxy radicals that contain $C_{3-6}$ cycloalkyl moieties.

As used herein, aryl radicals are selected from phenyl, naphthyl and indenyl.

As used herein, heteroaryl radicals contain from 3 to 10 members, preferably 5 or 6 members, including one or more heteroatoms selected from oxygen, sulfur and nitrogen. Examples of suitable 5 membered ring heteroaryl moieties include furyl, thiophenyl, pyrrolyl, imidazolyl, oxazolyl, thiazolyl, thienyl, tetrazolyl, and pyrazolyl. Examples of suitable 6 membered ring heteroaryl moieties include pyridinyl, pyrimidinyl, pyrazinyl, of which pyridinyl and pyrimidinyl are preferred.

As used herein, halogen is chlorine, iodine, fluorine or bromine.

As used herein, polycycloalkyl radicals are fused cyclic ring structures.

Representative polycycloalkyl radicals include, but are not limited to, adamantyl, bornanyl, norbornanyl, bornenyl and norbornenyl. Polycycloalkyl radicals can also include one or more heteroatoms, such as N, O or S.

As used herein, heterocyclyl radicals contain from 3 to 10 members including one or more heteroatoms selected from oxygen, sulfur and nitrogen. Examples of suitable heterocyclyl moieties include, but are not limited to, piperidinyl, morpholinyl, pyrrolidinyl, imidazolidinyl, pyrazolidinyl, isothiazolidinyl, thiazolidinyl, isoxazolidinyl, oxazolidinyl, piperazinyl, tetrahydropyranyl and tetrahydrofuranyl.

As used herein, cycloalkyl radicals contain from 3 to 8 carbon atoms. Examples of suitable cycloalkyl radicals include, but are not limited to, cyclopropyl, cyclobutyl, cyclopentyl, cyclohexyl, cycloheptyl and cyclooctyl.

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates. Representative salts are provided as described in U.S. Pat. No. 5,597,919 to Dull et al., U.S. Pat. No. 5,616,716 to Dull et al. and U.S. Pat. No. 5,663,356 to Ruecroft et al.

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partial agonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to a decrease in a particular effect or function that is induced by interaction of the antagonist with a binding partner, and can include allosteric effects.

As used herein, a "partial agonist" is a substance that provides a level of stimulation to its binding partner that is intermediate between that of a full or complete antagonist and an agonist defined by any accepted standard for agonist activity. It will be recognized that stimulation, and hence, inhibition is defined intrinsically for any substance or category of substances to be defined as agonists, antagonists, or partial agonists. As used herein, "intrinsic activity", or "efficacy," relates to some measure of biological effectiveness of the binding partner complex. With regard to receptor pharmacology, the context in which intrinsic activity or efficacy should be defined will depend on the context of the binding partner (e.g., receptor/ligand) complex and the consideration of an activity relevant to a particular biological outcome. For example, in some circumstances, intrinsic activity may vary depending on the particular second messenger system involved. See Hoyer, D. and Boddeke, H., Trends Pharmacol Sci. 14(7):270-5 (1993). Where such contextually specific evaluations are relevant, and how they might be relevant in the context of the present invention, will be apparent to one of ordinary skill in the art.

As used herein, neurotransmitters whose release is mediated by the compounds described herein include, but are not limited to, acetylcholine, dopamine, norepinephrine, serotonin and glutamate, and the compounds described herein function as agonists or partial agonists at one or more of the CNS nAChRs.

I. Compounds

The compounds of Formula (I) have one or more asymmetric carbons and can therefore exist in the form of isomers, racemic mixtures, enantiomers and diastereomers. These individual compounds and their mixtures are intended to be within the scope of the present invention.

The following are representative compounds of Formula (I):

(R)- and (S)-3-((E)-2-pyrrolidin-3-ylvinyl)-5-(tetrahydropyran-4-yloxy)pyridine (R)- and (S)-5-((E)-2-pyrrolidin-3-ylvinyl)pyrimidine (R)- and (S)-2-chloro-5-((E)-2-pyrrolidin-3-ylvinyl)pyridine (R)- and (S)-3-isopropoxy-5-((E)-2-pyrrolidin-3-ylvinyl)pyridine (R)- and (S)-3-isopropoxy-5-((E)-2-(1-methylpyrrolidin-3-yl)vinyl)pyridine (R)- and (S)-3-cyclopropylmethoxy-5-((E)-2-pyrrolidin-3-ylvinyl)pyridine (R)- and (S)-5-((E)-2-(1-methylpyrrolidin-3-yl)vinyl)pyrimidine (R)- and (S)-2-chloro-5-((E)-2-(1-methylpyrrolidin-3-yl)vinyl)pyridine (R)- and (S)-3-cyclopropylmethoxy-5-((E)-2-(1-methylpyrrolidin-3-yl)vinyl)pyridine (R)- and (S)-5-((E)-2-piperidin-3-ylvinyl)pyrimidine (R)- and (S)-5-((E)-2-(1-methylpiperidin-3-yl)vinyl)pyrimidine (R)- and (S)-2-chloro-5-((E)-2-piperidin-3-ylvinyl)pyridine (R)- and (S)-2-chloro-5-((E)-2-(1-methylpiperidin-3-yl)vinyl)pyridine (R)- and (S)-3-cyclopropylmethoxy-5-((E)-2-piperidin-3-ylvinyl)pyridine (R)- and (S)-3-cyclopropylmethoxy-5-((E)-2-(1-methylpiperidin-3-yl)vinyl)pyridine 5-((E)-2-piperidin-4-ylvinyl)pyrimidine 5-((E)-2-(1-methylpiperidin-4-yl)vinyl)pyrimidine 2-chloro-5-((E)-2-piperidin-4-ylvinyl)pyridine 2-chloro-5-((E)-2-(1-methylpiperidin-4-yl)vinyl)pyridine 3-cyclopropylmethoxy-5-((E)-2-piperidin-4-ylvinyl)pyridine 3-cyclopropylmethoxy-5-((E)-2-(1-methylpiperidin-4-yl)vinyl)pyridine 5-((E)-2-azetidin-3-ylvinyl)pyrimidine 5-((E)-2-(1-methylazetidin-3-yl)vinyl)pyrimidine 5-((E)-2-azetidin-3-ylvinyl)-2-chloropyridine 5-((E)-2-(1-methylazetidin-3-yl)vinyl)-2-chloropyridine
3-((E)-2-azetidin-3-ylvinyl)-5-cyclopropylmethoxypyridine
3-((E)-2-(1-methylazetidin-3-yl)vinyl)-5-cyclopropyl-methoxypyridine
(R)- and (S)-3-phenoxy-5-((E)-2-piperidin-3-ylvinyl)pyridine
(R)- and (S)-3-phenoxy-5-((E)-2-(1-methylpiperidin-3-yl)vinyl)pyridine
3-phenoxy-5-((E)-2-piperidin-4-ylvinyl)pyridine
3-phenoxy-5-((E)-2-(1-methylpiperidin-4-yl)vinyl)pyridine
3-phenoxy-5-((E)-2-azetidin-3-ylvinyl)pyridine and
3-phenoxy-5-((E)-2-(1-methylazetidin-3-yl)vinyl)pyridine.

In each of these compounds, individual isomers thereof, mixtures thereof, including racemic mixtures, enantiomers, diastereomers and tautomers thereof, and the pharmaceutically acceptable salts thereof, are intended to be within the scope of the present invention.

II. Compound Preparation

While other synthetic strategies will be apparent to those of skill in the art, the compounds of Formula (I) wherein $R^3$ represents a hydrogen can be obtained from a compound of general formula (II) in accordance with the following general synthesis scheme:

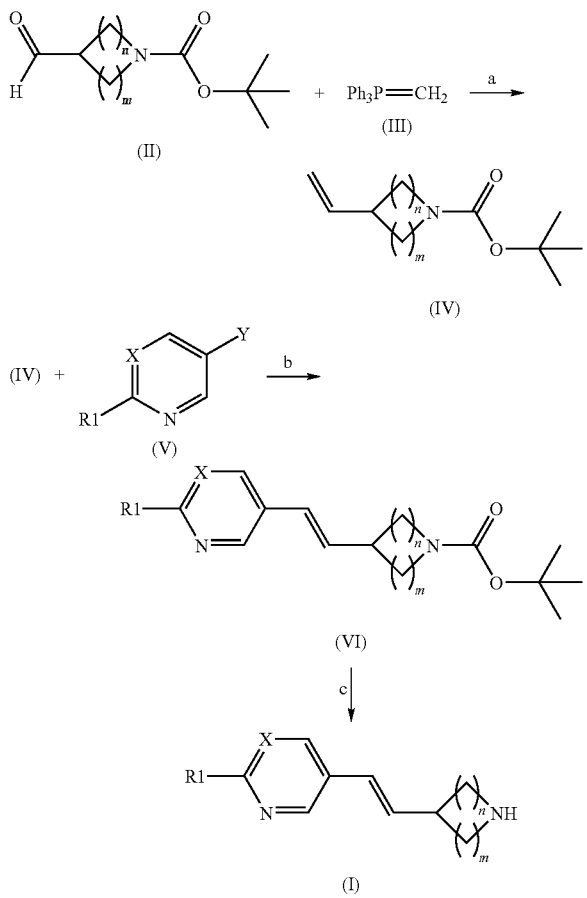

The general synthesis scheme is as follows:

a) an aldehyde of general formula (II) is reacted with the phosphorane ylide (III);

b) the vinylazacycloalkane of general formula (IV) is reacted with a heteroaryl halide of general formula (V, where Y=halogen);

c) the tert-butoxycarbonyl group is eliminated from the compound of general formula (VI);

and the product is isolated and optionally converted into a pharmaceutically acceptable salt.

The reaction (a) between an aldehyde of general formula (II) and the phosphorane ylide (III) advantageously takes place under an inert atmosphere (for example under nitrogen or argon) in an inert solvent such as tetrahydrofuran at a temperature between −10° C. and the boiling temperature of the reaction mixture, preferably at a temperature between around −5° C. and around 22° C.

The reaction (b) between a vinylazacycloalkane of general formula (IV) and an appropriate heteroaryl halide of general formula (V) advantageously takes place under an inert atmosphere in the presence of a catalyst such as palladium acetate, a base such as diisopropylethylamine and an inorganic salt such as lithium chloride, in an inert solvent such as dimethylformamide at a temperature between 20° C. and the boiling temperature of the reaction mixture. Ideally, the temperature of the reaction is in the region of about 110° C.

In another embodiment, the reaction (b) between a vinylazacycloalkane of general formula (IV) and an appropriate heteroaryl halide of general formula (V) can be performed preferably under an inert atmosphere (for example under nitrogen or under argon) in the presence of a catalyst such as palladium acetate and a phosphine such as triphenylphosphine in basic medium, for example in the presence of a base such as triethylamine, at a temperature between 20° C. and the boiling temperature of the reaction mixture, preferably at a temperature in the region of 110° C.

The reaction (c) takes place generally in accordance with the customary methods which do not adversely affect the rest of the molecule, in particular by applications of the methods described by T. W. Greene and P. G. M. Wuts, Protective Groups in Organic Synthesis (2nd ed.), A. Wiley—Interscience Publication (1991). For example, the reaction (c) of eliminating the tert-butoxycarbonyl group from the compound of general formula (VI) takes place preferably under an inert atmosphere (for example under nitrogen or under argon) in the presence of an acid such as trifluoroacetic acid in an inert solvent such as dichloromethane at a temperature between −10° C. and the boiling temperature of the reaction mixture, preferably at a temperature between −5° C. and a temperature in the region of 22° C.

Alternatively the reaction (c) of eliminating the tert-butoxycarbonyl group from the compound of general formula (VI) can be performed preferably under an inert atmosphere (for example under nitrogen or under argon) by the action of trimethylsilyl iodide in an inert solvent such as dichloromethane at a temperature between −10° C. and the boiling temperature of the reaction mixture, preferably at a temperature in the region of 22° C.

The derivatives of general formula (I) in which $R^3$ does not represent a hydrogen can be obtained from a compound of general formula (I) in which $R^3$ represents a hydrogen atom in accordance with the customary methods of amine alkylation which do not adversely affect the rest of the molecule, in particular by applications of the methods described by R. C. Larock, Comprehensive Organic Transformations, VCH Publishers (1989).

Alternatively the derivatives of general formula (I) in which $R^3$ represents a methyl can be obtained by reacting a compound of general formula (I) in which $R^3$ represents a hydrogen with a solution of formaldehyde in formic acid at a temperature between 22° C. and the boiling temperature of the reaction mixture.

The compounds of general formula (II) which are not commercially available can be obtained by applying or adapting methods described by Peschke B. et al., Eur. J. Med. Chem. 34:363-380 (1999), the contents of which are hereby incorporated by reference.

The compounds of general formula (V) which are not commercially available can be obtained by applying or adapting methods described in PCT WO 00/75110, the contents of which are hereby incorporated by reference. Alternatively the compounds of general formula (V) in which X is C—$R^2$;

$R^2$ is —$OR^6$; and $R^6$ is $C_{1-6}$ alkyl, aryl-$C_{1-6}$-alkyl, heteroaryl-$C_{1-6}$-alkyl, heterocyclyl, heterocyclylalkyl, cycloalkyl or polycycloalkyls, these radicals being optionally substituted by 1 or more substituents selected from halogen, $C_{1-6}$ alkyl, $C_{1-6}$ alkoxy, —CN, —$NO_2$, —$NH_2$, —OH, —COOH, —COO—$C_{1-6}$ alkyl, —$CONH_2$, formyl, trifluoromethyl or trifluoromethoxy, can be obtained from a heteroaryl halide of general formula (VII), where Y is a halogen and $R^1$ is as previously defined, and an alcohol of general formula (VIII), where $R^6$ is as previously defined, in accordance with the following general synthesis scheme:

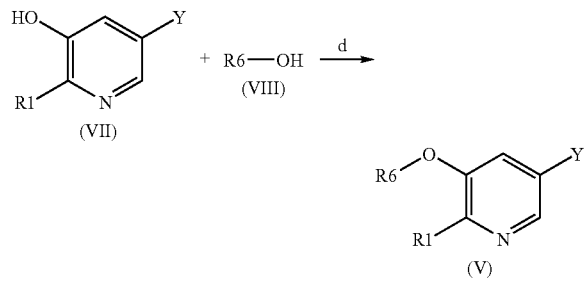

The reaction (d) between heteroaryl alcohol of general formula (VII) and an appropriate alcohol of general formula (VIII) takes place preferably under an inert atmosphere in the presence of a diazene such as diethyl azodicarboxylate and a phosphine such as triphenylphosphine in an inert solvent such as toluene at a temperature between 0° C. and the boiling temperature of the reaction mixture, preferably at a temperature between a temperature in the region of 22° C. and the boiling temperature of the solvent.

The compounds of general Formula (I) can be isolated and purified using methods well known to those of skill in the art, including, for example, crystallization, chromatography and/or extraction.

In the above-mentioned schemes, when any one or more of the R-groups are or contain reactive groups that are potentially reactive under the reaction conditions, for example, —OH, —SH, —$NH_2$ or —$CO_2H$, it will be readily apparent to those of skill in the art that these functional groups can require the use of suitable "protecting groups" during the reactions to "block" the reactivity of the R-group. These "protecting" groups can be chosen, introduced and cleaved in accordance to T. W. Greene and P. G. M. Wuts (Protective Groups in Organic Synthesis (2nd ed.), A. Wiley—Interscience Publication (1991)).

The compounds of general formula (I) and the compounds of general formula (IV) can be obtained in optically pure form by separating their racemates in accordance with the customary methods (i.e., resolution of enantiomers), or by using optically pure starting materials.

The compounds of general formula (I) can optionally be converted into addition salts with a mineral or organic acid by the action of such an acid in an appropriate solvent, for example, an organic solvent such as an alcohol, a ketone, an ether or a chlorinated solvent. These salts likewise form part of the invention.

Representative pharmaceutically acceptable salts include, but are not limited to, benzenesulfonate, bromide, chloride, citrate, ethanesulfonate, fumarate, gluconate, iodate, maleate, isethionate, methanesulfonate, methylenebis(β-oxynaphthoate), nitrate, oxalate, palmoate, phosphate, salicylate, succinate, sulfate, tartrate, theophyllinacetate, p-toluenesulfonate, hemigalactarate and galactarate salts.

III. Pharmaceutical Compositions

The pharmaceutical compositions according to the invention include a compound of Formula (I) or a salt thereof, in the pure state or in the form of a composition in which it is combined with any other pharmaceutically compatible product, which can be inert or physiologically active. Such compositions can be administered, for example, orally, parenterally, rectally or topically.

Examples of solid compositions for oral administration include, but are not limited to, tablets, pills, powders (gelatin capsules, cachets) and granules. In these compositions, the active compound is mixed with one or more inert diluents, such as starch, cellulose, sucrose, lactose or silica, ideally under a stream of an inert gas such as argon.

The compositions can also include substances other than diluents, for example, one or more lubricants such as magnesium stearate or talc, a colorant, a coating (coated tablets) or a varnish.

Examples of liquid compositions for oral administration include, but are not limited to, solutions, suspensions, emulsions, syrups and elixirs that are pharmaceutically acceptable and typically contain inert diluents such as water, ethanol, glycerol, vegetable oils or liquid paraffin. These compositions can comprise substances other than the diluents, for example, wetting agents, sweeteners, thickeners, flavors and stabilizers.

Sterile compositions for parenteral administration can include, for example, aqueous or nonaqueous solutions, suspensions and emulsions. Examples of suitable solvents and vehicles include, but are not limited to aqueous solutions, preferably buffered aqueous solutions, propylene glycol, a polyethylene glycol, vegetable oils, especially olive oil, injectable organic esters, for example ethyl oleate, and other appropriate organic solvents. These compositions can also include adjuvants, especially wetting agents, isotonicity agents, emulsifiers, dispersants and stabilizers. Such sterile compositions can be sterilized in a number of ways, for example, by aseptizicing filtration, by incorporating sterilizing agents into the composition, by irradiation and by heating. They can also be prepared in the form of sterile solid compositions which can be dissolved at the time of use in sterile water or any other sterile injectable medium.

Examples of compositions for rectal administration include, but are not limited to, suppositories and rectal capsules that, in addition to the active product, can include excipients such as cocoa butter, semi-synthetic glycerides and polyethylene glycols.

Compositions for topical administration can, for example, be creams, lotions, eyewashes, collutoria, nasal drops or aerosols.

The pharmaceutical compositions also can include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, anticoagulants, buffering agents, anti-inflammatory agents, antipyretics, time release binders, anesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition. In certain circumstances, a compound of the present invention can be employed as part of a pharmaceutical composition with other compounds intended to prevent or treat a particular disorder.

IV. Methods of Treatment

The compounds described herein are useful for treating those types of conditions and disorders for which other types of nicotinic compounds have been proposed as therapeutics. See, for example, Williams et al., DN&P 7(4):205-227 (1994), Arneric et al., CNS Drug Rev. 1(1):1-26 (1995), Arneric et al., Exp. Opin. Invest. Drugs 5(1):79-100 (1996), Bencherif et al., J. Pharmacol. Exp. Ther. 279:1413 (1996), Lippiello et al., J. Pharmacol. Exp. Ther. 279:1422 (1996), Damaj et al., Neuroscience (1997), Holladay et al., J. Med. Chem. 40(28): 4169-4194 (1997), Bannon et al., Science 279: 77-80 (1998), PCT WO 94/08992, PCT WO 96/31475, and U.S. Pat. No. 5,583,140 to Bencherif et al., U.S. Pat. No. 5,597,919 to Dull et al., and U.S. Pat. No. 5,604,231 to Smith et al.

The compounds can also be used as adjunct therapy in combination with existing therapies in the management of the aforementioned types of diseases and disorders. In such situations, it is preferably to administer the active ingredients in a manner that minimizes effects upon nAChR subtypes such as those that are associated with muscle and ganglia. This can be accomplished by targeted drug delivery and/or by adjusting the dosage such that a desired effect is obtained without meeting the threshold dosage required to achieve significant side effects. The pharmaceutical compositions can be used to ameliorate any of the symptoms associated with those conditions, diseases and disorders.

Examples of conditions and disorders that can be treated include neurological disorders, neurodegenerative disorders, in particular, CNS disorders, and inflammatory disorders. CNS disorders can be drug induced; can be attributed to genetic predisposition, infection or trauma; or can be of unknown etiology. CNS disorders comprise neuropsychiatric disorders, neurological diseases and mental illnesses, and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a deficiency of choline, dopamine, norepinephrine and/or serotonin.

Examples of CNS disorders that can be treated using the compounds of Formula (I) and their pharmaceutically acceptable salts, and pharmaceutical compositions including these compounds, include pre-senile dementia (early onset Alzheimer's disease), senile dementia (dementia of the Alzheimer's type), Lewy Body dementia, micro-infarct dementia, AIDS-related dementia, HIV-dementia, multiple cerebral infarcts, Parkinsonism including Parkinson's disease, Pick's disease, progressive supranuclear palsy, Huntington's chorea, tardive dyskinesia, hyperkinesia, epilepsy, mania, attention deficit disorder, anxiety, depression, dyslexia, schizophrenia depression, obsessive-compulsive disorders, Tourette's syndrome, mild cognitive impairment (MCI), age-associated memory impairment (AAMI), premature amnesic and cognitive disorders which are age-related or a consequence of alcoholism, or immunodeficiency syndrome, or are associated with vascular disorders, with genetic alterations (such as, for example, trisomy 21) or with attention deficiencies or learning deficiencies, acute or chronic neurodegenerative conditions such as amyotrophic lateral sclerosis, multiple sclerosis, peripheral neurotrophies, and cerebral or spinal traumas. In addition, the compounds can be used to treat nicotine addiction and/or other behavioral disorders related to substances that lead to dependency (e.g., alcohol, cocaine, heroin and opiates, psychostimulants, benzodiazepines and barbiturates). The compounds can also be used to treat pathologies exhibiting an inflammatory character within the gastrointestinal system such as Crohn's disease, irritable bowel syndrome and ulcerous colitis, and in diarrheas.

The manner in which the compounds are administered can vary. The compounds can be administered by inhalation (e.g., in the form of an aerosol either nasally or using delivery articles of the type set forth in U.S. Pat. No. 4,922,901 to Brooks et al.); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; intracerebroventricularly; or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time-release capsule. As another example, the compounds can be delivered transdermally using the types of patch technologies available from Novartis and Alza Corporation. The administration of the pharmaceutical compositions of the present invention can be intermittent, or at a gradual, continuous, constant or controlled rate to a warm-blooded animal, (e.g., a mammal such as a mouse, rat, cat, rabbit, dog, pig, cow, or monkey); but advantageously is preferably administered to a human being. In addition, the time of day and the number of times per day that the pharmaceutical formulation is administered can vary. Administration preferably is such that the active ingredients of the pharmaceutical formulation interact with receptor sites within the body of the subject that affect the functioning of the CNS or of the gastrointestinal (GI) tract. More specifically, in treating a CNS disorder administration preferably is such so as to optimize the effect upon those relevant receptor subtypes which have an effect upon the functioning of the CNS, while minimizing the effects upon muscle-type receptor subtypes. Other suitable methods for administering the compounds of the present invention are described in U.S. Pat. No. 5,604,231 to Smith et al., the disclosure of which is incorporated herein by reference in its entirety.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. Thus, when treating a CNS disorder, an effective amount of compound is an amount sufficient to pass across the blood-brain barrier of the subject, to bind to relevant receptor sites in the brain of the subject, and to activate relevant nicotinic receptor subtypes (e.g., provide neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the recurrence of the symptoms of the disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to activate relevant receptors to effect neurotransmitter (e.g., dopamine) release but the amount should be insufficient to induce effects on skeletal muscles and ganglia to any significant degree. The effective dose of compounds will of course differ from patient to patient but in general includes amounts starting where CNS effects or other desired therapeutic effects occur, but below the amount where muscular effects are observed.

The doses depend on the desired effect, the duration of treatment and the administration route used; they are generally between 0.05 mg and 100 mg of active substance per day orally for an adult.

Generally speaking, the doctor will determine the appropriate dosage as a function of the age, weight and all the other factors specific to the patient.

The compounds preferably have the ability to pass across the blood-brain barrier of the patient. As such, such compounds have the ability to enter the central nervous system of the patient. The log P values of typical compounds, which are useful in carrying out the present invention are generally greater than about 0, often are greater than about 0.5, and frequently are greater than about 1. The log P values of such typical compounds generally are less than about 3.5, often are less than about 3, and sometimes are less than about 2.5. Log P values provide a measure of the ability of a compound to pass across a diffusion barrier, such as a biological membrane. See, Hansch, et al., J. Med. Chem. 11:1 (1968).

The compounds have the ability to bind to, and in most circumstances, cause activation of, nAChRs of the brain of the patient (e.g., such as those receptors that modulate dopamine release). As such, such compounds have the ability to express nicotinic pharmacology, and in particular, to act as nicotinic agonists or partial agonists. The receptor binding constants of typical compounds useful in carrying out the present invention generally exceed about 0.1 nM, often exceed about 1 nM, and frequently exceed about 10 nM. The receptor binding constants of such typical compounds generally are less than about 1 μM, often are less than about 100 nM, and frequently are less than about 50 nM. Receptor binding constants provide a measure of the ability of the compound to bind to half of the relevant receptor sites of certain brain cells of the patient. See, Cheng, et al., Biochem. Pharmacol. 22:3099 (1973).

The compounds useful according to the method of the present invention have the ability to demonstrate a nicotinic function by effectively eliciting ion flux through, and/or neurotransmitter secretion from, nerve ending preparations (e.g., thalamic or striatal synaptosomes). As such, such compounds have the ability to cause relevant neurons to become activated, and to release or secrete acetylcholine, dopamine, or other neurotransmitters. Generally, typical compounds useful in carrying out the present invention effectively provide for relevant receptor activation in amounts of at least about 30 percent, often at least about 50 percent, and frequently at least about 75 percent, of that maximally provided by (S)-(−)-nicotine. Generally, typical compounds useful in carrying out the present invention are more potent than (S)-(−)-nicotine in eliciting relevant receptor activation. Generally, typical compounds useful in carrying out the present invention effectively provide for the secretion of dopamine in amounts of at least about 50 percent, often at least about 75 percent, and frequently at least about 100 percent, of that maximally provided by (S)-(−)-nicotine. Certain compounds of the present invention can provide secretion of dopamine in an amount which can exceed that maximally provided by (S)-(−)-nicotine. Generally, typical compounds useful in carrying out the present invention are less potent than (S)-(−)-nicotine in eliciting neurotransmitter secretion, such as dopamine secretion.

The compounds of the present invention, when employed in effective amounts in accordance with the method of the present invention, lack the ability to elicit activation of nAChRs of human muscle to any significant degree. In that regard, the compounds of the present invention demonstrate poor ability to cause isotopic rubidium ion flux through nAChRs in cell preparations expressing muscle-type nicotinic acetylcholine receptors. Thus, such compounds exhibit receptor activation constants or EC50 values (i.e., which provide a measure of the concentration of compound needed to activate half of the relevant receptor sites of the skeletal muscle of a patient) which are extremely high (i.e., greater than about 100 μM). Generally, typical preferred compounds useful in carrying the present invention activate isotopic rubidium ion flux by less than 10 percent, often by less than 5 percent, of that maximally provided by S(−) nicotine.

The compounds of the present invention, when employed in effective amounts in accordance with the method of the present invention, lack the ability to elicit activation of human ganglion nAChRs to any significant degree. This selectivity of the compounds of the present invention against those nAChRs responsible for cardiovascular side effects is demonstrated by a lack of the ability of those compounds to activate nicotinic function of adrenal chromaffin tissue. As such, such compounds have poor ability to cause isotopic rubidium ion flux through nAChRs in cell preparations derived from the adrenal gland. Generally, typical preferred compounds useful in carrying out the present invention maximally activate isotopic rubidium ion flux by less than 10 percent, often by less than 5 percent, of that maximally provided by S(−) nicotine.

The compounds are effective towards providing some degree of prevention of the progression of CNS disorders, ameliorating the symptoms of CNS disorders, and ameliorating to some degree the recurrence of CNS disorders. However, such effective amounts of those compounds are not sufficient to elicit any appreciable undesired nicotinic effects, as is demonstrated by decreased effects on preparations believed to reflect effects on the cardiovascular system, or effects to skeletal muscle. As such, administration of compounds of the present invention provides a therapeutic window in which treatment of certain CNS disorders is provided, and undesired peripheral nicotinic effects/side effects are avoided. That is, an effective dose of a compound of the present invention is sufficient to provide the desired effects upon the CNS, but is insufficient (i.e., is not at a high enough level) to provide undesirable side effects. Preferably, effective administration of a compound of the present invention resulting in treatment of CNS disorders occurs upon administration of less than ⅓, frequently less than ⅕, and often less than ⅒, that amount sufficient to cause any side effects to a significant degree.

SYNTHETIC EXAMPLES

The following synthetic examples are provided to illustrate the present invention, and should not be construed as limiting thereof. In these examples, all parts and percentages are by weight, unless otherwise noted. Reaction yields are reported in mole percentages.

Example 1

Racemic 3-((E)-2-Pyrrolidin-3-ylvinyl)-5-(tetrahydropyran-4-yloxy)pyridine hemigalactarate Trifluoroacetic acid (0.91 cm$^3$, 11.7 mmol) was added drop-wise to a solution of 0.44 g (1.17 mmol) of racemic 3-{(E)-2-[5-(tetrahydropyran-4-yloxy)pyridin-3-yl]vinyl}pyrrolidine-1-carboxylic acid tert-butyl ester in 4.5 cm$^3$ of dichloromethane, which was under argon and was cooled to 0° C. The reaction mixture was stirred at this temperature for 0.5 h and then at a temperature in the region of 22° C. for 20 h and was concentrated to dryness under reduced pressure (2.7 kPa). The oily residue was taken up in 5 cm$^3$ of water and the resulting solution was rendered basic (pH=8) by adding 28% aqueous ammonia solution and then extracted with 3 times 25 cm$^3$ of dichloromethane. The combined organic phases were washed with 25 cm$^3$ of water, dried over magnesium sulfate, filtered and concentrated to dryness under reduced pressure (2.7 kPa) to give 0.225 g of orange-colored oil, which was purified by chromatography on silica gel [eluent: dichloromethane/methanol (9/1 then 8/2 by volume)]. Concentration of the fractions under reduced pressure (2.7 kPa) gave 0.1 g (0.36 mmol) of orange-colored oil. Galactaric acid (0.038 g, 0.18 mmol) was added to a solution of this oil in 2 cm$^3$ of methanol to which 0.5 cm$^3$ of water has been added. The mixture was brought to reflux and cooled to a temperature in the region of 22° C. and the insoluble material was removed by filtration. The filtrate was concentrated to dryness under reduced pressure (2.7 kPa) and the oily residue was taken up in 2 cm$^3$ of ethanol. The precipitated solid was filtered off, washed with 2 cm$^3$ of isopropyl acetate and 2 cm$^3$ of diisopropyl ether and then dried at 40° C. under vacuum (2.7 kPa) to give 0.088 g of racemic 3-((E)-2-pyrrolidin-3-ylvinyl)-5-(tetrahydropyran-4-yloxy)pyridine hemigalactarate in the form of a beige solid. Mass spectrum (EI): m/z 274 (M+), m/z 232. 1H NMR spectrum (300 MHz, (CD$_3$)$_2$SO d6 with a few drops of CD$_3$COOD d4, δ in ppm): 1.61 (m: 2H); 1.82 (m: 1H); 1.98 (m: 2H); 2.17 (m: 1H); 2.96 (dd, J=10.5 and 8.5 Hz: 1H); 3.07 (m: 1H); from 3.10 to 3.40 (m: 2H); 3.41 (dd, J=10.5 and 7.5 Hz: 1H); 3.50 (ddd, J=12–9.5 and 3 Hz: 2H); 3.79 (s: 1H); 3.87 (dt, J=12 and 4.5 Hz: 2H); 4.24 (s: 1H); 4.69 (m: 1H); 6.43 (dd, J=16 and 7 Hz: 1H); 6.56 (d, J=16 Hz: 1H); 7.49 (m: 1H); 8.20 (m: 2H).

Racemic 3-{(E)-2-[5-(tetrahydropyran-4-yloxy)pyridin-3-yl]vinyl}pyrrolidine-1-carboxylic acid tert-butyl ester can be Prepared as Follows Palladium acetate (0.117 g, 0.52 mmol), 0.678 g (16 mmol) of lithium chloride and 7.25 cm$^3$ (42 mmol) of ethyldiisopropylamine were added in succession to a solution under argon of 1.33 g (5.17 mmol) of 3-bromo-5-(tetrahydropyran-4-yloxy)pyridine and 1.2 g (5.17 mmol) of racemic 3-vinylpyrrolidine-1-carboxylic acid tert-butyl ester in 15 cm$^3$ of dimethylformamide. After 3 hours of heating at 110° C. with stirring, the reaction mixture was stirred for 2 hours at a temperature in the region of 22° C. and then concentrated to dryness under reduced pressure (2.7 kPa). The oily residue was taken up in 50 cm$^3$ of ethyl acetate and the resulting solution was washed in succession with 2 times 25 cm$^3$ of water, 25 cm$^3$ of saturated bicarbonate solution, 2 times 25 cm$^3$ of water and 25 cm$^3$ of saturated sodium chlorine solution and then was dried over magnesium sulfate, filtered and concentrated to dryness under reduced pressure (2.7 kPa) to give 1.4 g of brown oil. This residue was purified by chromatography on silica gel [eluent: cyclohexane/ethyl acetate (8/2 by volume)]. Concentration of the fractions under reduced pressure (2.7 kPa) gave 0.44 g of yellow oil which was used without further purification in the remainder of the synthesis.

3-Bromo-5-(tetrahydropyran-4-yloxy)pyridine can be prepared as follows:

Diethyl azodicarboxylate (7.1 cm$^3$, 45 mmol) was added drop-wise to a solution under argon of 5.22 g (30 mmol) of 5-bromopyridin-3-ol, 4.69 g (45 mmol) of tetrahydropyran-4-ol (45 mmol) and 11.8 g (45 mmol) of triphenylphosphine in 150 cm$^3$ of toluene. After 20 hours of heating under reflux with stirring, the reaction mixture was brought to a temperature in the region of 22° C. and then washed in succession with 2 times 75 cm$^3$ of water, 2 times 75 cm$^3$ of saturated bicarbonate solution, 2 times 75 cm$^3$ of water and 75 cm$^3$ of saturated sodium chloride solution and then the organic solution was dried over magnesium sulfate, filtered and concentrated to dryness under reduced pressure (2.7 kPa) to give an orange-colored oil. This residue was admixed with 100 cm$^3$ of diisopropyl ether and the solid formed was filtered off and washed with 2 times 25 cm$^3$ of diisopropyl ether. The filtrate was concentrated to dryness under reduced pressure (2.7 kPa) to give 10 g of an orange-colored oil. This residue was purified by chromatography on silica gel [eluent: cyclohexane/ethyl acetate (8/2 by volume)]. Concentration of the fractions under reduced pressure (2.7 kPa) gave 7.3 g of 3-bromo-5-(tetrahydropyran-4-yloxy)pyridine in the form of a yellow oil. 1H NMR spectrum (300 MHz, (CD$_3$)$_2$SO d6, δ in ppm): 1.59 (m: 2H); 1.99 (m: 2H); 3.49 (ddd, J=12.5-9.5 and 3 Hz: 2H); 3.87 (dt, J=12.5 and 4.5 Hz: 2H); 4.75 (m: 1H); 7.82 (dd, J=2.5 and 2 Hz: 1H); 8.28 (d, J=2 Hz: 1H); 8.33 (d, J=2.5 Hz: 1H).

Racemic 3-vinylpyrrolidine-1-carboxylic acid tert-butyl ester can be prepared as follows:

n-Butyllithium in hexane (44 cm$^3$ of a 1.6 N solution) was added drop-wise to a suspension of 25.5 g (71 mmol) of triphenylmethylphosphonium bromide in 300 cm$^3$ of tetrahydrofuran, which was under argon and cooled to 0° C. The reaction mixture was stirred at 0° C. for 0.5 h and then admixed with a solution of 7.1 g (35.6 mmol) of racemic 3-formylpyrrolidine-1-carboxylic acid tert-butyl ester in 100 cm$^3$ of tetrahydrofuran. After 2.5 hours of reaction at a temperature in the region of 22° C., the mixture was poured into 600 cm$^3$ of saturated aqueous ammonium chloride solution. Following addition of ethyl acetate the organic phase was taken off by decanting, washed twice with water and with saturated sodium chloride solution and then dried over magnesium sulfate and concentrated to dryness under reduced pressure (2.7 kPa). The resulting oil was purified by chromatography on silica gel [eluent: cyclohexane/ethyl acetate (95/5 then 9/1 by volume)]. Concentration of the fractions under reduced pressure (2.7 kPa) gave 6.3 g of racemic 3-vinylpyrrolidine-1-carboxylic acid tert-butyl ester in the form of a colorless oil. Mass spectrum (ES): m/z 198 (MH+), m/z=142.

Example 2

Racemic 5-((E)-2-pyrrolidin-3-ylvinyl)pyrimidine hemigalactarate

Trifluoroacetic acid (1.2 cm$^3$, 15.6 mmol) was added dropwise to a solution of 0.43 g (1.56 mmol) of racemic 3-((E)-2-pyrimidin-5-ylvinyl)pyrrolidine-1-carboxylic acid tert-butyl ester in 6 cm3 of dichloromethane, which was under argon and cooled to 0° C. The reaction mixture was stirred at this temperature for 0.5 h then at a temperature in the region of 22° C. for 20 hours and it was concentrated to dryness under reduced pressure (2.7 kPa). The oily residue was taken up in 5 cm$^3$ of water and the resulting solution was rendered basic (pH=8) by adding 28% aqueous ammonia solution and was then extracted with 3 times 25 cm$^3$ of dichloromethane. The combined organic phases were washed with 25 cm$^3$ of water, dried over magnesium sulfate, filtered and concentrated to dryness under reduced pressure (2.7 kPa) to give 0.126 g of orange-colored oil which was purified by chromatography on silica gel [eluent: dichloromethane/methanol (9/1 then 8/2 by volume)]. Concentration of the fractions under reduced pressure (2.7 kPa) gave 0.1 g (0.57 mmol) of orange-colored oil. Galactaric acid (0.06 g, 0.28 mmol) was added to a solution of this oil in 2 cm$^3$ of methanol to which 0.5 cm$^3$ of water has been added. The mixture was brought to reflux and cooled to a temperature in the region of 22° C. and the insoluble material was removed by filtration. The filtrate was concentrated to dryness under reduced pressure (2.7 kPa) and the oily residue was taken up in 2 cm$^3$ of ethanol. The precipitated solid was filtered off, washed with 2 cm$^3$ of isopropyl acetate and 2 cm$^3$ of diisopropyl ether and then dried at 40° C. under vacuum (2.7 kPa) to give 0.1 g of racemic 5-((E)-2-pyrrolidin-3-ylvinyl)pyrimidine hemigalactarate in the form of an ochre solid. Mass spectrum (DCI): m/z 176 (MH+). 1H NMR spectrum (300 MHz, (CD$_3$)$_2$SO d6 with a few drops of CD$_3$COOD d4, δ in ppm): 1.82 (m: 1H); 2.18 (m: 1H); 2.98 (dd, J=11 and 8.5 Hz: 1H); 3.10 (m: 1H); 3.20 (m: 1H); 3.33 (m: 1H); 3.42 (dd, J=11 and 7.5 Hz: 1H); 3.79 (s: 1H); 4.24 (s: 1H); 6.55 (limit AB: 2H); 8.87 (s: 2H); 9.04 (s: 1H).

Racemic 3-((E)-2-pyrimidin-5-ylvinyl)pyrrolidine-1-carboxylic acid tert-butyl ester can be prepared as follows:

Palladium acetate (0.117 g, 0.52 mmol), 0.678 g (16 mmol) of lithium chloride and 7.25 cm$^3$ (42 mmol) of ethyldiisopropylamine were added in succession to a solution under argon of 0.822 g (5.17 mmol) of 5-bromopyrimidine and 1.2 g (5.17 mmol) of racemic 3-vinylpyrrolidine-1-carboxylic acid tert-butyl ester in 15 cm$^3$ of dimethylformamide. After 3 hours of heating at 110° C. with stirring, the reaction mixture was stirred for 2 hours at a temperature in the region of 22° C. and then concentrated to dryness under reduced pressure (2.7 kPa). The oily residue was taken up in 50 cm$^3$ of ethyl acetate and the resulting solution was washed in succession with 2 times 25 cm$^3$ of water, 25 cm$^3$ of saturated bicarbonate solution, 2 times 25 cm$^3$ of water and 25 cm$^3$ of saturated sodium chloride solution and was then dried over magnesium sulfate, filtered and concentrated to dryness under reduced pressure (2.7 kPa) to give 1.1 g of brown oil. This residue was purified by chromatography on silica gel [eluent: cyclohexane/ethyl acetate (8/2 by volume)]. Concentration of the fractions under reduced pressure (2.7 kPa) gave 0.43 g of racemic 3-((E)-2-pyrimidin-5-ylvinyl)pyrrolidine-1-carboxylic acid tert-butyl ester in the form of an oil. 1H NMR spectrum (300 MHz, (CD$_3$)$_2$SO d6, δ in ppm): 1.42 (s: 9H); 1.78 (m: 1H); 2.05 (m: 1H); from 2.90 to 3.15 (m: 2H); from 3.15 to 3.60 (m: 3H); 6.51 (d, J=16.5 Hz: 1H); 6.64 (dd, J=16.5 and 7 Hz: 1H); 8.89 (s: 2H); 9.04 (s: 1H).

Example 3

(+)-5-((E)-2-Pyrrolidin-3-ylvinyl)pyrimidine galactarate

Trimethylsilyl iodide (0.2 cm$^3$, 1.4 mmol) was added at a temperature in the region of 22° C. to a solution under argon of 0.26 g (0.944 mmol) of (+)-3-((E)-2-pyrimidin-5-ylvinyl)pyrrolidine-1-carboxylic acid tert-butyl ester in 10 cm$^3$ of dichloromethane. After 2 hours of stirring at this temperature the reaction mixture was admixed with 15 cm$^3$ of 5% aqueous ammonia solution and stirred for 1 hour at a temperature in the region of 22° C. and left to settle. The aqueous phase was separated and extracted with dichloromethane. The combined organic phases were washed twice with water and with saturated aqueous sodium chloride solution and were then dried over magnesium sulfate, filtered and concentrated to dryness under reduced pressure (2.7 kPa) to give 0.06 g of orange-colored oil. Galactaric acid (0.035 g, 0.16 mmol) was added to a solution of this oil in 6 cm$^3$ of methanol to which 0.6 cm$^3$ of water has been added. The mixture was brought to reflux, cooled to a temperature in the region of 22° C. and concentrated to dryness under reduced pressure (2.7 kPa). The oily residue was triturated in the presence of 5 cm$^3$ of diisopropyl ether and the solid formed was filtered off and then dried at 45° C. under vacuum (2.7 kPa) to give 0.072 g of (+)-5-((E)-2-pyrrolidin-3-ylvinyl)pyrimidine galactarate in the form of a yellow solid. Mass spectrum (DCI): m/z=176 (MH+). $^1$H NMR spectrum (300 MHz, (CD$_3$)$_2$SO d6 with a few drops of CD$_3$COOD d4, δ in ppm): 1.81 (m: 1H); 2.19 (m: 1H); 2.98 (dd, J=11 and 9 Hz: 1H); 3.10 (m: 1H); 3.21 (m: 1H); 3.33 (m: 1H); 3.43 (dd, J=11 and 8 Hz: 1H); 3.79 (s: 2H); 4.25 (s: 2H); 6.56 (limit AB: 2H); 8.88 (s: 2H); 9.05 (s: 1H).

(+)-3-((E)-2-Pyrimidin-5-ylvinyl)pyrrolidine-1-carboxylic acid tert-butyl ester can be prepared as follows:

A racemic mixture of 3-((E)-2-pyrimidin-5-ylvinyl)pyrrolidine-1-carboxylic acid tert-butyl ester (0.5 g) was injected in two parts on a 8 cm diameter column containing 1.2 kg of chiral stationary phase Chiralpak AS TM 20 μm [flow: 130 ml/min, eluent: heptane/methanol/ethanol (98/1/1 by volume)]. Concentration of the fractions under reduced pressure (2.7 kPa) gave 0.24 g of (+)-((E)-2-Pyrimidin-5-ylvinyl)pyrrolidine-1-carboxylic acid tert-butyl ester and 0.27 g of (−)-((E)-2-Pyrimidin-5-ylvinyl)pyrrolidine-1-carboxylic acid tert-butyl ester. (+)-((E)-2-Pyrimidin-5-ylvinyl)pyrrolidine-1-carboxylic acid tert-butyl ester was eluted in first position with a retention time of 14.2 min on a 4.6 mm diameter and 250 mm length Chiralpak AS TM 20 μm column [flow: 1 ml/min, eluent: heptane/methanol/ethanol (98/1/1 by volume)]. $^1$H NMR spectrum (300 MHz, (CD$_3$)$_2$SO d6, δ in ppm): 1.43 (s: 9H); 1.79 (m: 1H); 2.06 (m: 1H); from 2.95 to 3.15 (m: 2H); from 3.20 to 3.35 (m: 1H); 3.44 (ddd, J=11-8.5 and 3 Hz: 1H); 3.53 (broad dd, J=10 and 7.5 Hz: 1H); 6.52 (d, J=16.5 Hz: 1H); 6.63 (dd, J=16.5 and 7 Hz: 1H); 8.89 (s: 2H); 9.04 (s: 1H).

(−)-((E)-2-Pyrimidin-5-ylvinyl)pyrrolidine-1-carboxylic acid tert-butyl ester was eluted in second position with a retention time of 17 min on a 4.6 mm diameter and 250 mm length Chiralpak AS TM 20 μm column [flow: 1 ml/min, eluent: heptane/methanol/ethanol (98/1/1 by volume)]. $^1$H NMR spectrum (300 MHz, (CD$_3$)$_2$SO d6, δ in ppm): 1.43 (s: 9H); 1.79 (m: 1H); 2.06 (m: 1H); from 2.95 to 3.15 (m: 2H); from 3.20 to 3.35 (m: 1H); 3.44 (ddd, J=11-8.5 and 3 Hz: 1H);

3.53 (broad dd, J=10 and 7.5 Hz: 1H); 6.52 (d, J=16.5 Hz: 1H); 6.63 (dd, J=16.5 and 7 Hz: 1H); 8.89 (s: 2H); 9.04 (s: 1H).

Example 4

(−)-5-((E)-2-Pyrrolidin-3-ylvinyl)pyrimidine galactarate

Trimethylsilyl iodide (0.2 cm$^3$, 1.4 mmol) was added at a temperature in the region of 22° C. to a solution under argon of 0.29 g (1.053 mmol) of (−)-3-((E)-2-pyrimidin-5-ylvinyl)pyrrolidine-1-carboxylic acid tert-butyl ester in 10 cm$^3$ of dichloromethane. After 2 hours of stirring at this temperature the reaction mixture was admixed with 15 cm$^3$ of 5% aqueous ammonia solution, stirred for 1 h at a temperature in the region of 22° C. and left to settle. The aqueous phase was separated off and extracted with dichloromethane. The combined organic phases were washed twice with water and with saturated aqueous sodium chloride solution and then were dried over magnesium sulfate, filtered and concentrated to dryness under reduced pressure (2.7 kPa) to give 0.1 g of orange-colored oil. Galactaric acid (0.06 g, 0.28 mmol) was added to a solution of this oil in 10 cm3 of methanol to which 1 cm$^3$ of water has been added. The mixture was brought to reflux, cooled to a temperature in the region of 22° C. and concentrated to dryness under reduced pressure (2.7 kPa). The oily residue was triturated in the presence of 5 cm$^3$ of diisopropyl ether and the solid formed was filtered and then dried at 45° C. under vacuum (2.7 kPa) to give 0.094 g of (−)-5-((E)-2-pyrrolidin-3-ylvinyl)pyrimidine galactarate in the form of a yellow solid. Mass spectrum (DCI): m/z=176 (MH+). $^1$H NMR spectrum (300 MHz, (CD$_3$)$_2$SO d6 with a few drops of CD$_3$COOD d4, δ in ppm): 1.82 (m: 1H); 2.19 (m: 1H); 2.98 (dd, J=11 and 9 Hz: 1H); 3.10 (m: 1H); 3.21 (m: 1H); 3.32 (m: 1H); 3.43 (dd, J=11 and 7.5 Hz: 1H); 3.79 (s: 2H); 4.24 (s: 2H); 6.57 (limit AB: 2H); 8.88 (s: 2H); 9.05 (s: 1H).

(−)-3-((E)-2-Pyrimidin-5-ylvinyl)pyrrolidine-1-carboxylic acid tert-butyl ester can be prepared as described in Example 3.

Example 5

Determination of Log P Value

Log P values, which have been used to assess the relative abilities of compounds to pass across the blood-brain barrier (Hansch, et al., J. Med. Chem. ii:1 (1968)), were calculated using the Cerius$^2$ software package Version 3.5 by Molecular Simulations, Inc.

Example 6

Evaluation of the Various Properties of Representative Compounds

The following assays were be used to determine the binding affinity and other pharmacological properties of certain of the compounds described herein, and can be used, generally, to evaluate other compounds as described herein.

Radioligand Binding at Central Nervous System n-Acetylcholine Receptors (CNS nAChR)

α4β2 Subtype

Rats (female, Sprague-Dawley), weighing 150-250 g, were maintained on a 12 h light/dark cycle and were allowed free access to water and food supplied by PMI Nutrition International, Inc. Animals were anesthetized with 70% CO$_2$, then decapitated. Brains were removed and placed on an ice-cold platform. The cerebral cortex was removed and placed in 20 volumes (weight:volume) of ice-cold preparative buffer (NaCl, 137 mM; KCl, 10.7 mM; KH2PO4, 5.8 mM; Na$_2$HPO$_4$, 8 mM; HEPES (free acid), 20 mM; iodoacetamide, 5 mM; EDTA, 1.6 mM; pH 7.4); PMSF, dissolved in methanol to a final concentration of 100 μM, was added, and the suspension was homogenized by Polytron. The homogenate was centrifuged at 18,000×g for 20 min at 4° C. and the resulting pellet was re-suspended in 20 volumes of ice-cold water. After 60 min. incubation on ice, a new pellet was collected by centrifugation at 18,000×g for 20 min at 4° C. The final pellet was re-suspended in 10 volumes of buffer and stored at −20° C. On the day of the assay, tissue was thawed, centrifuged at 18,000×g for 20 min, then re-suspended in ice-cold PBS (Dulbecco's Phosphate Buffered Saline, NaCl, 138 mM; KCl, 2.67 mM; KH$_2$PO$_4$, 1.47 mM; Na$_2$HPO$_4$, 8.1 mM; CaCl$_2$, 0.9 mM; MgCl$_2$, 0.5 mM; Invitrogen/Gibco; pH 7.4) to a final concentration of approximately 4 mg protein/mL. Protein was determined by the method of Lowry et al., J. Biol. Chem. 193: 265-275 (1951), using bovine serum albumin as the standard.

The binding of [$^3$H]nicotine was measured using a modification of the methods of Romano et al., Science 210: 647-650 (1980) and Marks et al., Mol. Pharmacol. 30: 427-436 (1986). The [$^3$H]nicotine (Specific Activity=81.5 Ci/mmol) was obtained from NEN Research Products. The binding of [$^3$H]nicotine was measured using a 3 hr. incubation at 4° C. Incubations were conducted in 48-well micro-titre plates and contained about 400 μg of protein per well in a final incubation volume of 300 μL. The incubation buffer was PBS and the final concentration of [$^3$H]nicotine was 5 nM. The binding reaction was terminated by filtration of the protein containing bound ligand onto glass fiber filters (GF/B, Brandel) using a Brandel Tissue Harvester at 4° C. Filters were soaked in de-ionized water containing 0.33% polyethyleneimine to reduce non-specific binding. Each filter was washed 3 times with 1 mL of ice-cold buffer. Non-specific binding was determined by inclusion of 10 μM non-radioactive L-nicotine (Acros Organics) in selected wells.

The inhibition of [$^3$H]nicotine binding by test compounds was determined by including seven different concentrations of the test compound in selected wells. Each concentration was replicated in triplicate. IC$_{50}$ values were estimated as the concentration of compound that inhibited 50 percent of specific [$^3$H]nicotine binding. Inhibition constants (Ki values), reported in nM, were calculated from the IC$_{50}$ values using the method of Cheng et al., Biochem. Pharmacol. 22: 3099-3108 (1973).

α7 Subtype

Rats (female, Sprague-Dawley), weighing 150-250 g, were maintained on a 12 h light/dark cycle and were allowed free access to water and food supplied by PMI Nutrition International, Inc. Animals were anaesthetized with 70% CO$_2$, then decapitated. Brains were removed and placed on an ice-cold platform. The hippocampus was removed and placed in 10 volumes (weight:volume) of ice-cold preparative buffer (NaCl, 137 mM; KCl, 10.7 mM; KH$_2$PO$_4$, 5.8 mM; Na$_2$HPO$_4$, 8 mM; HEPES (free acid), 20 mM; iodoacetamide, 5 mM; EDTA, 1.6 mM; pH 7.4); PMSF, dissolved in methanol to a final concentration of 100 μM, was added, and the tissue suspension was homogenized by Polytron. The homogenate was centrifuged at 18,000×g for 20 min at 4° C. and the resulting pellet was re-suspended in 10 volumes of ice-cold water. After 60 min incubation on ice, a new pellet was collected by centrifugation at 18,000×g for 20 min at 4° C. The final pellet was re-suspended in 10 volumes of buffer and stored at −20° C. On the day of the assay, tissue was thawed, centrifuged at 18,000×g for 20 min, then re-suspended in ice-cold PBS (Dulbecco's Phosphate Buffered Saline, NaCl, 138 mM; KCl, 2.67 mM; KH$_2$PO$_4$, 1.47 mM; Na$_2$HPO$_4$, 8.1 mM; CaCl$_2$, 0.9 mM; MgCl$_2$, 0.5 mM; Invitrogen/Gibco; pH 7.4) to a final concentration of approximately 2 mg protein/mL. Protein was determined by the method of Lowry et al., J. Biol. Chem. 193: 265-275 (1951), using bovine serum albumin as the standard.

The binding of [$^3$H]MLA was measured using a modification of the methods of Davies et al., Neuropharmacol. 38: 679-690, 1999). [$^3$H]MLA (Specific Activity=25-35 Ci/mmol) was obtained from Tocris. The binding of [$^3$H] MLA was determine using a 2 h incubation at 21° C. Incubations were conducted in 48-well micro-titre plates and contained 300 g of protein per well in a final incubation volume of about 200 μL. The incubation buffer was PBS and the final concentration of [$^3$H]MLA was 5 nM. The binding reaction was terminated by filtration of the protein containing bound ligand onto glass fiber filters (GF/B, Brandel) using a Brandel Tissue Harvester at room temperature. Filters were soaked in de-ionized water containing 0.33% polyethyleneimine to reduce non-specific binding. Each filter was washed 3 times with 1 mL of PBS at room temperature. Non-specific binding was determined by inclusion of 50 μM nonradioactive MLA in selected wells.

The inhibition of [$^3$H]MLA binding by test compounds was determined by including seven different concentrations of the test compound in selected wells. Each concentration was replicated in triplicate. $IC_{50}$ values were estimated as the concentration of compound that inhibited 50 percent of specific [$^3$H]MLA binding. Inhibition constants (Ki values), reported in nM, were calculated from the $IC_{50}$ values using the method of Cheng et al., Biochem. Pharmacol. 22: 3099-3108 (1973).

Determination of Dopamine Release

Dopamine release was measured using striatal synaptosomes obtained from rat brain, according to the procedures set forth by Rapier et al., J. Neurochem. 54: 937-45 (1990). Rats (female, Sprague-Dawley), weighing 150-250 g, were maintained on a 12 h light/dark cycle and were allowed free access to water and food supplied by PMI Nutrition International, Inc. Animals were anaesthetized with 70% $CO_2$, then decapitated. The brains were quickly removed and the striata dissected. Striatal tissue from 2 rats was pooled and homogenized in 5 ml of ice-cold 0.32 M sucrose containing 5 mM HEPES, pH 7.4, using a glass/glass homogenizer. The tissue was then centrifuged at 1,000×g for 10 minutes. The pellet was discarded and the supernatant was centrifuged at 12,000 g for 20 minutes. The resulting pellet was resuspended in perfusion buffer containing monoamine oxidase inhibitors (128 mM NaCl, 1.2 mM $KH_2PO_4$, 2.4 mM KCl, 3.2 mM $CaCl_2$, 1.2 mM $MgSO_4$, 25 mM HEPES, 1 mM ascorbic acid, 0.02 mM pargyline HCl and 10 mM glucose, pH 7.4) and centrifuged for 15 minutes at 25,000 g. The final pellet was resuspended in 1.4 ml perfusion buffer for immediate use.

The synaptosomal suspension was incubated for 10 minutes at 37° C. to restore metabolic activity. [$^3$H]Dopamine ([$^3$H]DA, specific activity=28.0 Ci/mmol, NEN Research Products) was added at a final concentration of 0.1 μM and the suspension was incubated at 37° C. for another 10 minutes. 50 μL aliquots of tissue+100 μL perfusion buffer were loaded into the suprafusion chambers of a Brandel Suprafusion System (series 2500, Gaithersburg, Md.). Perfusion buffer (room temperature) was pumped into the chambers at a rate of 3 ml/min for a wash period of 8 minutes. Test compound (10 μM) or nicotine (10 μM) was then applied in the perfusion stream for 40 seconds. Fractions (12 seconds each) were continuously collected from each chamber throughout the experiment to capture basal release, agonist-induced peak release and to re-establish the baseline after the agonist application. The perfusate was collected directly into scintillation vials, to which scintillation fluid was added. [$^3$H]DA released was quantified by scintillation counting. For each chamber, the integrated area of the peak was normalized to its baseline.

Release was expressed as a percentage of release obtained with an equal concentration of L-nicotine. Within each assay, each test compound was replicated using 2-3 chambers; replicates were averaged. When appropriate, dose-response curves of test compound were determined. The maximal activation for individual compounds ($E_{max}$) was determined as a percentage of the maximal activation induced by L-nicotine. The compound concentration resulting in half maximal activation ($EC_{50}$) of specific ion flux was also defined.

Selectivity vs. Peripheral nAChRs

Interaction at the Human Muscle Subtype

Activation of muscle-type nAChR was established on the human clonal line TE671/RD, which is derived from an embryonal rhabdomyosarcoma (Stratton et al., Carcinogen 10: 899-905, 1989). These cell express receptors that have pharmacological (Lukas et al., J. Pharmacol. Exp. Ther. 251: 175-182, 1989), electrophysiological (Oswald et al., Neurosci. Lett. 96: 207-212; 1989), and molecular biological profiles (Luther et al., J. Neurosci. 9: 1082-1096, 1989) similar to the muscle-type nAChR.

TE671/RD cells were maintained in proliferative growth phase according to routine protocols (Bencherif et al., Mol. Cell. Neurosci. 2: 52-65 (1991) and Bencherif et al., J. Pharmacol. Exp. Ther. 257: 946-953 (1991)). Cells were cultured in Dulbecco's modified Eagle's medium (Gibco/BRL) with 10% horse serum (Gibco BRL), 5% fetal bovine serum (HyClone, Logan Utah), 1 mM sodium pyruvate, 4 mM L-Glutamine, 50,000 units penicillin-streptomycin (Irvine Scientific). When cells were 80% confluent, they were plated to 6 well polystyrene plates (Costar). Experiments were conducted when the cells reached 100% confluency.

Nicotinic acetylcholine receptor (nAChR) function was assayed using $^{86}Rb^+$ efflux according to a method described by Lukas et al., Anal. Biochem. 175: 212-218 (1988). On the day of the experiment, growth media was gently removed from the well and growth media containing $^{86}$Rubidium chloride ($10^6$ Ci/ml) was added to each well. Cells were incubated at 37° C. for a minimum of 3 hours. After the loading period, excess $^{86}$Rb was removed and the cells were washed twice with label-free Dulbecco's phosphate buffered saline (NaCl, 138 mM; KCl, 2.67 mM; $KH_2PO_4$, 1.47 mM; $Na_2HPO_4$, 8.1 mM; $CaCl_2$, 0.9 mM; $MgCl_2$, 0.5 mM; Invitrogen/Gibco, pH. 7.4), taking care not to disturb the cells. Next, cells were exposed to 100 μM of test compound, or 100 μM of L-nicotine (Acros Organics), or buffer alone for 4 minutes. Following the exposure period, the supernatant containing the released $^{86}$Rb was removed and transferred to scintillation vials. Scintillation fluid was added and released radioactivity was measured by liquid scintillation counting.

Within each assay, each point had 2 replicates, which were averaged. The amount of $^{86}$Rb release was compared to both a positive control (100 μM L-nicotine) and a negative control (buffer alone) to determine the percent release relative to that of L-nicotine.

When appropriate, dose-response curves of test compound were determined. The maximal activation for individual compounds ($E_{max}$) was determined as a percentage of the maximal activation induced by L-nicotine. The compound concentration resulting in half maximal activation ($EC_{50}$) of specific ion flux was also defined.

Interaction at the Rat Ganglionic Subtype

Activation of the rat ganglion nAChR were established on the pheochromocytoma clonal line PC12, which is a continuous clonal cell line of neural crest origin, derived from a tumor of the rat adrenal medulla. These cells express ganglion-like neuronal nAChRs (see Whiting et al., Nature 327: 515-518 (1987); Lukas et al., J. Pharmacol. Exp. Ther. 251: 175-182 (1989); Whiting et al., Mol. Brain. Res. 10: 61-70 (1990)).

Rat PC12 cells were maintained in proliferative growth phase according to routine protocols (Bencherif et al., Mol. Cell. Neurosci. 2: 52-65 (1991) and Bencherif et al., J. Pharmacol. Exp. Ther. 257: 946-953 (1991)). Cells were cultured in Dulbecco's modified Eagle's medium (Gibco/BRL) with 10% horse serum (Gibco BRL), 5% fetal bovine serum (HyClone, Logan Utah), 1 mM sodium pyruvate, 4 mM L-Glutamine, 50,000 units penicillin-streptomycin (Irvine Scientific). When cells were 80% confluent, they were plated to 6 well Nunc plates (Nunclon), coated with 0.03% poly-L-lysine (Sigma, dissolved in 100 mM boric acid). Experiments were conducted when the cells reached 80% confluency.

Nicotinic acetylcholine receptor (nAChR) function was assayed using $^{86}Rb^+$ efflux according to a method described by Lukas et al., Anal. Biochem. 175: 212-218 (1988). On the day of the experiment, growth media was gently removed from the well and growth media containing $^{86}$Rubidium chloride ($10^6$ Ci/ml) was added to each well. Cells were incubated at 37° C. for a minimum of 3 hours. After the loading period, excess $^{86}Rb$ was removed and the cells were washed twice with label-free Dulbecco's phosphate buffered saline (NaCl, 138 mM; KCl, 2.67 mM; $KH_2PO_4$, 1.47 mM; $Na_2HPO_4$, 8.1 mM; $CaCl_2$, 0.9 mM; $MgCl_2$, 0.5 mM; Invitrogen/Gibco, pH. 7.4), taking care not to disturb the cells. Next, cells were exposed to 100 µM of test compound, or 100 µM of nicotine, or buffer alone for 4 minutes. Following the exposure period, the supernatant containing the released $^{86}Rb^+$ was removed and transferred to scintillation vials. Scintillation fluid was added and released radioactivity was measured by liquid scintillation counting.

Within each assay, each point had 2 replicates, which were averaged. The amount of $^{86}Rb$ release was compared to both a positive control (100 µM nicotine) and a negative control (buffer alone) to determine the percent release relative to that of L-nicotine.

When appropriate, dose-response curves of test compound were determined. The maximal activation for individual compounds ($E_{max}$) was determined as a percentage of the maximal activation induced by L-nicotine. The compound concentration resulting in half maximal activation ($EC_{50}$) of specific ion flux was also defined.

Interaction at the Human Ganglionic Subtype

The cell line, SH-SY5Y, is a continuous line derived by sequential subcloning of the parental cell line, SK-N-SH, which was originally obtained from a human peripheral neuroblastoma. SH-SY5Y cells express a ganglion-like nAChR (Lukas et al., Mol. Cell. Neurosci. 4: 1-12, 1993).

Human SHSY5Y cells were maintained in proliferative growth phase according to routine protocols (Bencherif et al., Mol. Cell. Neurosci. 2: 52-65 (1991) and Bencherif et al., J. Pharmacol. Exp. Ther. 257: 946-953 (1991)). Cells were cultured in Dulbecco's modified Eagle's medium (Gibco/BRL) with 10% horse serum (Gibco BRL), 5% fetal bovine serum (HyClone, Logan Utah), 1 mM sodium pyruvate, 4 mM L-Glutamine, 50,000 units penicillin-streptomycin (Irvine Scientific). When cells were 80% confluent, they were plated to 6 well polystyrene plates (Costar). Experiments were conducted when the cells reached 100% confluency.

Nicotinic acetylcholine receptor (nAChR) function was assayed using $^{86}Rb^+$ efflux according to a method described by Lukas et al., Anal. Biochem. 175: 212-218 (1988). On the day of the experiment, growth media was gently removed from the well and growth media containing $^{86}$Rubidium chloride ($10^6$ Ci/ml) was added to each well. Cells were incubated at 37° C. for a minimum of 3 hours. After the loading period, excess $^{86}Rb^+$ was removed and the cells were washed twice with label-free Dulbecco's phosphate buffered saline (NaCl, 138 mM; KCl, 2.67 mM; $KH_2PO_4$, 1.47 mM; $Na_2HPO_4$, 8.1 mM; $CaCl_2$, 0.9 mM; $MgCl_2$, 0.5 mM; Invitrogen/Gibco, pH. 7.4), taking care not to disturb the cells. Next, cells were exposed to 100 µM of test compound, or 100 µM of nicotine, or buffer alone for 4 minutes. Following the exposure period, the supernatant containing the released $^{86}Rb$ was removed and transferred to scintillation vials. Scintillation fluid was added and released radioactivity was measured by liquid scintillation counting.

Within each assay, each point had 2 replicates, which were averaged. The amount of $^{86}Rb$ release was compared to both a positive control (100 µM nicotine) and a negative control (buffer alone) to determine the percent release relative to that of L-nicotine.

When appropriate, dose-response curves of test compound were determined. The maximal activation for individual compounds ($E_{max}$) was determined as a percentage of the maximal activation induced by L-nicotine. The compound concentration resulting in half maximal activation ($EC_{50}$) of specific ion flux was also defined.

Representative compounds were evaluated using the assays described herein. The results indicate that the compounds of the present invention selectively bind at α4β2 nAChRs and consequently elicit dopamine release. Typically, Ki values for binding at α4β2 are in the range 1-100 nM, and $E_{max}$ values for dopamine release approach 100% of that produced by nicotine. In contrast, the compounds of the present invention do not bind well at those subtypes of the nAChR which are characteristic of the peripheral nervous and muscular systems. Thus, the compounds of the present invention possess therapeutic potential in treating central nervous system disorders without producing side effects associated with interaction with the peripheral nervous system.

Having disclosed the subject matter of the present invention, it should be apparent that many modifications, substitutions and variations of the present invention are possible in light thereof. It is to be understood that the present invention can be practiced other than as specifically described. Such modifications, substitutions and variations are intended to be within the scope of the present application.

What is claimed is:

1. A compound

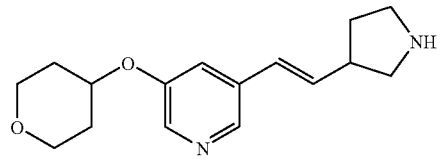

or a pharmaceutically acceptable salt thereof.

2. A pharmaceutical composition comprising a compound of claim 1 and a pharmaceutically acceptable carrier.

* * * * *